United States Patent
Arras et al.

(10) Patent No.: US 10,239,984 B2
(45) Date of Patent: Mar. 26, 2019

(54) PROCESS FOR THE PRODUCTION OF DI- AND POLYAMINES OF THE DIPHENYLMETHANE SERIES

(71) Applicant: Covestro Deutschland AG, Leverkusen (DE)

(72) Inventors: Jürgen Arras, Itzehoe (DE); Stefan Wershofen, Mönchengladbach (DE); Javier Pérez-Ramirez, Zürich (CH); Tobias Caesar Keller, Bremgarten (CH)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 0 days.

(21) Appl. No.: 15/323,999

(22) PCT Filed: Jul. 2, 2015

(86) PCT No.: PCT/EP2015/065124
§ 371 (c)(1),
(2) Date: Jan. 5, 2017

(87) PCT Pub. No.: WO2016/005269
PCT Pub. Date: Jan. 14, 2016

(65) Prior Publication Data
US 2017/0158798 A1   Jun. 8, 2017

(30) Foreign Application Priority Data
Jul. 7, 2014   (EP) ..................... 14175927

(51) Int. Cl.
| C08G 12/00 | (2006.01) |
| C07C 209/78 | (2006.01) |
| C08G 12/08 | (2006.01) |
| C07C 209/54 | (2006.01) |
| B01J 29/08 | (2006.01) |
| B01J 29/70 | (2006.01) |
| B01J 29/18 | (2006.01) |
| B01J 29/00 | (2006.01) |

(52) U.S. Cl.
CPC .............. *C08G 12/08* (2013.01); *B01J 29/08* (2013.01); *B01J 29/18* (2013.01); *B01J 29/70* (2013.01); *B01J 29/7007* (2013.01); *C07C 209/54* (2013.01); *C07C 209/78* (2013.01); *Y02P 20/582* (2015.11)

(58) Field of Classification Search
CPC .................................................... C08G 12/00
USPC ........................................................ 528/238
See application file for complete search history.

(56) References Cited

U.S. PATENT DOCUMENTS

| 3,362,979 A | 1/1968 | Bentley |
| 3,860,637 A | 1/1975 | Bentley |
| 3,971,829 A | 7/1976 | Marquis |
| 4,039,580 A | 8/1977 | Frulla et al. |
| 4,039,581 A | 8/1977 | Frulla et al. |
| 4,092,343 A | 5/1978 | Frulla et al. |
| 4,294,987 A | 10/1981 | Prather et al. |
| 6,380,433 B1 | 4/2002 | Perego et al. |
| 6,649,798 B2 | 11/2003 | Klein et al. |
| 6,936,737 B2 | 8/2005 | De Angelis et al. |
| 7,105,700 B2 | 9/2006 | De Angelis et al. |
| 7,115,537 B2 | 10/2006 | Perego et al. |
| 8,558,027 B2 | 10/2013 | Weiner et al. |
| 8,871,979 B2 | 10/2014 | Mitchell et al. |

FOREIGN PATENT DOCUMENTS

| BE | 1013456 A6 | 2/2002 |
| CN | 101259419 A | 9/2008 |
| CZ | 301977 B6 | 8/2010 |
| EP | 0264744 A2 | 4/1988 |
| EP | 0329367 A2 | 8/1989 |
| JP | 2012-131720 A | 7/2012 |
| JP | 2012-250971 A | 12/2012 |
| JP | 2013-095724 A | 5/2013 |
| WO | 03082803 A1 | 10/2003 |

OTHER PUBLICATIONS

Salzinger, Michael et al; "Reaction network and mechanism of the synthesis of methylenedianiline over dealuminated Y-type zeolites"; Green Chemistry; (2011); 13; pp. 149-155.
Simmler, Walter; "Silicon Compounds, Inorganic"; Ullmann's Encyclopedia of Industrial Chemistry; (2000); DOI: 10.1002/14356007.a24_001.
Mitchell, Sharon et al; "From powder to technical body: the undervalued science of catalyst scale up"; Chem. Soc. Rev.; (2013); 42; pp. 6094-6112.
Verboekend, Danny et al; "Hierarchy Brings Function: Mesoporous Clinoptilolite and L Zeolite Catalysts Synthesized by Tandem Acid-Base Treatments"; Chemistry of Materials; (2013); 25; pp. 1947-1959.
Salzinger, Michael et al; "On the influence of pore geometry and acidity on the activity of parent and modified zeolites in the synthesis of methylenedianiline"; Applied Catalysis A: General; Elsevier Science B.V.; 393; (2011); pp. 189-194.

(Continued)

*Primary Examiner* — Duc Truong
(74) *Attorney, Agent, or Firm* — N. Denise Brown

(57) ABSTRACT

The invention relates to a production process for polyamines through condensation of aromatic amines with formaldehyde employing at least one solid zeolite catalyst partially or fully ion-exchanged to the protonic form which has been A) alkaline-treated, wherein the alkaline treatment is in case of BEA zeolites carried out in the presence of a pore-directing agent and in case of zeolites other than BEA zeolites in the presence or absence of a pore-directing agent, or B) acid-treated without any alkaline treatment preceding or following said acid treatment, wherein the acid treatment is effected with an organic acid with chelating function.

14 Claims, No Drawings

(56) References Cited

OTHER PUBLICATIONS

Holm Spangsberg, Martin et al; "Catalysis with hierarchical zeolites"; Catalysis Today; Elsevier Science B.V.; (2011); 168; pp. 3-16.

Perez-Ramirez, Javier et al; "Hierarchical zeolites: enhanced utilisation of micropourous crystals in catalysis by advances in materials design"; Chemical Society Reviews; 37; (2008); pp. 2530-2542.

Perego, Carlo et al; "Amorphous aluminosilicate catalysts for hydroxyalklation of aniline and phenol"; Applied Catalysts; A: General; (2006); Elsevier Science B.V.; 307; pp. 128-136.

Corma, Avelino et al; "Preparation, characterisation and catalytic activity of ITQ-2, a delaminated zeolite"; Microporous and Mesoporous Materials; Elsevier Science B.V.; 38; (2000); pp. 301-309.

Corma, A.; "MWW MCM-22 Si(94), Al(6)"; Verified Syntheses of Zeolitic Materials; Elsevier Science B.V.; (2001); 2nd edition; pp. 225-227.

Zamecheck, W.; "Determination of the elemental compositor of zeolitic materials"; Verified Syntheses of Zeolitic Materials (Eds: H. Robson and K. P. Lillerund); Elsevier Science B.V.; Elsevier Science B.V.; (2001); 2nd edition; pp. 51-53.

Kugita, Tsuyoshi et al; "Catalytic activity of zeolites for synthesis reaction of methylenedianiline from aniline and formaldehyde"; Catalysis Today; 111; (2006); pp. 275-279.

De Angelis, Alberto et al; "Solid Acid Catalysts for Industrial Condensations of Ketones and Aldehydes with Aromatics"; Ind. Eng. Chem. Res.; (2004); 43; pp. 1169-1178.

Corma, Avelino et al; "Replacing HCl by solid acids in industrial processes: synthesis of diamino diphenyl methan (DADPM) for producing polyurethanes"; Chem. Comm.; (2004); pp. 2008-2010.

Botella, P. et al; "Towards an industrial synthesis of diamino diphenyl methan (DADPM) using novel delaminated materials: A breakthrough step in the production of isocyanates for polyurethanes"; Applied Catalysis A: General 398; (2011); pp. 143-149.

Verboekend, Danny et al; "Design of hierarchical zeolite catalysts by desilication"; Catal. Sci. Technol.; (2011); 1; pp. 879-890.

PROCESS FOR THE PRODUCTION OF DI- AND POLYAMINES OF THE DIPHENYLMETHANE SERIES

CROSS-REFERENCE TO RELATED APPLICATIONS

This application is a national stage application under 35 U.S.C. § 371 of PCT/EP2015/065124, filed Jul. 2, 2015, which claims the benefit of European Application No. 14175927.4, filed Jul. 7, 2014, both of which are incorporated by reference herein.

FIELD

The invention relates to a production process for polyamines through condensation of aromatic amines with formaldehyde employing at least one solid zeolite catalyst partially or fully ion-exchanged to the protonic form which has been
A) alkaline-treated, wherein the alkaline treatment is in case of BEA zeolites carried out in the presence of a pore-directing agent and in case of zeolites other than BEA zeolites in the presence or absence of a pore-directing agent,
or
B) acid-treated without any alkaline treatment preceding or following said acid treatment, wherein the acid treatment is effected with an organic acid with chelating function.

BACKGROUND

Diamines and polyamines of the diphenylmethane series (MDA) are understood to be amines and mixtures of amines of the following formula (I):

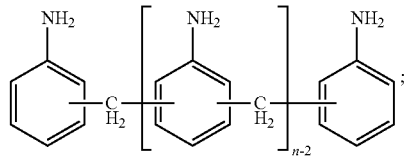

wherein n represents a natural number ≥2.

For compounds and mixtures of compounds with n=2, the term "monomeric MDA" (hereinafter MMDA) is also conventionally used, whilst compounds and mixtures of compounds with n>2 are conventionally referred to as "polymeric MDA" (PMDA). For the sake of simplicity, mixtures containing compounds with n=2 and n>2 side by side are hereinafter referred to as MDA (diamines and poly amines of the diphenylmethane series).

The most important isomers of MMDA are 4,4'-MDA, 2,4'-MDA and 2,2'-MDA:

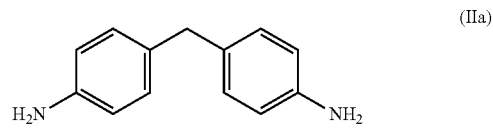

4,4'-MDA

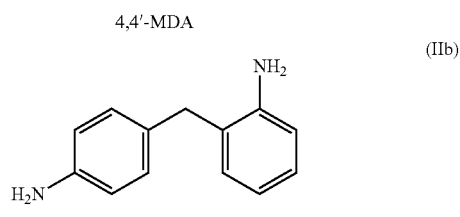

2,4'-MDA

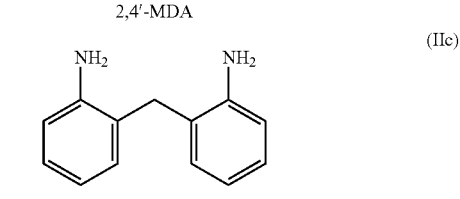

2,2'-MDA 4,4'-MDA is sometimes called the para-isomer, whereas both 2,4'-MDA and 2,2'-MDA individually or grouped together are sometimes referred to as ortho-isomers.

As a synonym for the PMDA, the terms "higher homologues of MDA" and "oligomers of MDA" can be found in the literature.

MDA is an extremely suitable starting material from which—optionally after further purification—the respective di- and polyisocyanates (hereinafter MDI) that represent an important raw product for polyurethane systems, for example, can be obtained by phosgenation. At the same time, the aliphatic systems that are obtained from MDA by hydrogenation of the aromatic ring also play an important role as paint resins.

Of the many conceivable methods described in the literature for the production of MDA, manufacture from the aniline-formaldehyde condensation product (known as aminal) is the most important because it is the most economically advantageous. This process can be illustrated in idealised form by means of the following diagram:

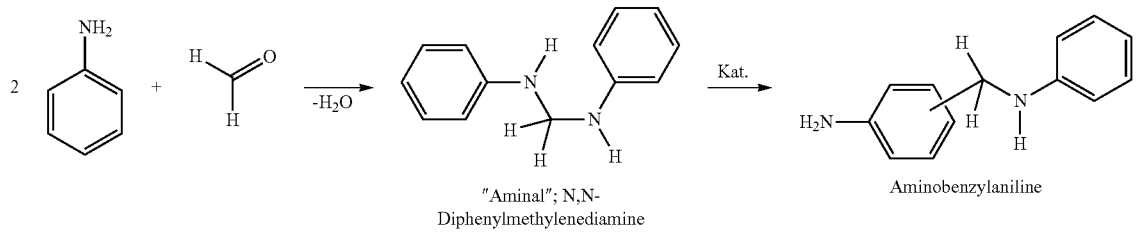

"Aminal"; N,N-Diphenylmethylenediamine

Aminobenzylaniline

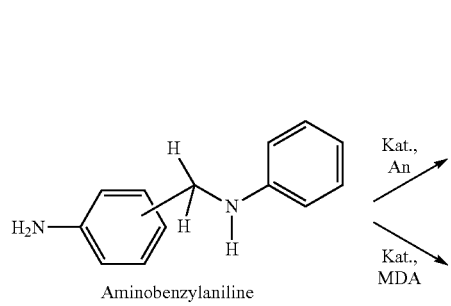

Aminobenzylaniline

Kat., An

Kat., MDA

-continued

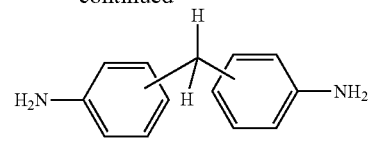

Monomeric-MDA

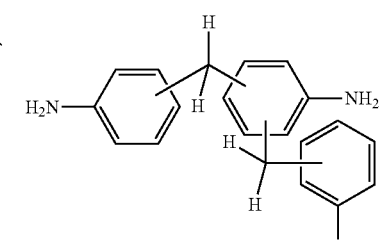

Polymeric-MDA
(polynuclear)

Depending on the variant, the condensation product (the "aminal") is produced first and then rearranged in the presence of a catalyst; alternatively, the condensation itself is performed in the presence of a catalyst under rearrangement conditions.

The rearrangement is catalysed by acids. Usually, solutions of strong acids, such as hydrochloric acid, sulfuric acid, and/or phosphoric acid, are employed in either variant, giving rise to the formation of an amine salt, which generally is subsequently neutralized with a base. For this purpose, strong bases such as sodium hydroxide are frequently used. This process suffers from several disadvantages:

Obviously, large quantities of strong acid are required, which is undesirable from an economic as well as an ecological perspective. In addition, use of strong acids may necessitate use of corrosion resistant materials in the equipment. Such construction materials are often expensive. Furthermore, neutralization of the strong acids employed with bases inevitably leads to the formation of large quantities of salts, which must be disposed of safely. These salts may also be contaminated with organic products, which need to be discharged, resulting in increased production costs. Additionally, substantial quantities of waste water are generated by this process, requiring additional processing capacity for the further treatment of the waste water before this can be safely discharged into a sewerage system.

A whole series of suggestions for the industrial implementation of the rearrangement has therefore already been made in order to overcome these disadvantages. Generally, the approach is taken to substitute mineral acids such as hydrochloric acid by solid acids, thereby simplifying the separation of MDA and catalyst as well as, at least in principle, allowing to reuse the catalyst.

However, a feasible method for the production of MDA avoiding mineral acids must meet the following conditions, for example:
a) Quantitative yields: an intermediate-free (aminobenzylaniline-free) product must be obtained in order to ensure that it is capable of being phosgenated (these can be extremely troublesome in the subsequent processing of the MDA to MDI (phosgenation).
b) Isomer distribution: similarly to the mineral acid-catalysed method, the product composition must be able to be controlled to some extent by varying the process parameters.
c) Service life: a catalyst used in industry must achieve an economic service life with high space-time yields before its activity can be restored by means of regeneration.
d) Foreign substances: the catalyst used must release no trace components in the product that have a negative influence on product quality. In addition, the method must cause no foreign matter, e.g. in the form of a solvent that is foreign to the system, to be brought into the reaction mixture.

Clays such as attapulgite and kaolin are stable up to 180° C. and can be regenerated through calcination (cf. U.S. Pat. Nos. 4,039,580, 4,092,343 and 4,294,987). However, in the production of MDA they exhibit a low selectivity to the 4,4'-isomer (the ratio of 4,4'-MMDA to 2,4'-MMDA being approximately of from 2 to 4), as a result of their weak acidity. The intolerance to water in the feed (max. 0.15 wt.-%) is a further drawback in industrial application, since a distillation of the intermediate aminal to reduce the water content is cost-prohibitive.

In contrast, amorphous silica-alumina (ASA) materials provide higher activities, an increased water tolerance (up to 3 wt.-%), and stronger acid sites, leading to improved selectivity, the ratio of 4,4'-MMDA to 2,4'-MMDA being approximately 5 (cf. U.S. Pat. Nos. 3,362,979, 3,971,829 and BE1013456A6). However, an even higher ratio of para to ortho isomers would be desirable.

It is known from U.S. Pat. No. 3,860,637 that rearrangement of the aminal using amorphous silicon-aluminium-mixed oxide cracking catalysts results in high yields of 4,4'-isomers when the reaction is performed in the presence of added ortho-isomers. These preferentially react to higher oligomers of MDA. A high proportion of PMDA is therefore conventionally obtained, which has to be separated from the desired 4,4'-isomer. This process requires the additional step of recycling the ortho-isomers initially formed.

A general problem of catalysts in MDA synthesis is deactivation due to inefficient removal of reaction products (Alberto de Angelis et al., *Ind. Eng. Chem. Res.*, 2004, 43, 1169-1178). Accordingly, highly mesoporous silica-alumina samples such as MCM-41 have been tested (Carlo Perego et al., *Appl. Catal., A*, 2006, 307, 128-136). However, selectivity was not sufficiently high, and the synthesis of the catalysts is costly.

WO 2010/019844 discloses the application of solid acid silica-metal oxide catalysts in the synthesis of MDA. The conversion is below 100% with ABA concentration of >1%.

Zeolites provide strong Brønsted-acid sites resulting from tetrahedrally coordinated aluminium incorporated in the crystalline framework. Additionally, zeolites can provide shape selectivity. Compared to other zeolites, Faujasite (FAU) and beta (BEA) zeolites have been described as most active catalysts in MDA synthesis (Tsuyoshi Kugita, et al., Catal. Today, 2006, 111, 275-279. Zeolite beta was identified as the most active zeolite, but provided an undesirably low para/ortho ratio of about 2.5, which was attributed to shape-selective properties of the zeolite micropores (Avelino Corma et al., Chem. Commun., 2004, 2008-2010).

EP 1 055 663 B1 discloses the use of zeolitic materials with a spaciousness index between 2.5 and 19 for catalysing aminal rearrangement with high conversion above 95% to MDA. BEA is mentioned as preferred framework.

Silanized solid materials having a spaciousness index between 2.5 and 19 are disclosed in EP 1 355 874 B1 as catalysts for MDA synthesis. The ratios of 4,4'- to 2,4'-MDA described therein are, depending on the catalyst, between 1.15 and 3.7. Silanization is rather ecologically unfriendly since the utilized precursor tetraorthosilicate have to be produced from pure silicon over silicon tetrachloride as intermediate (Inorganic Silicon Compounds, W. Simmler in Ullmann's Encyclopedia of Industrial Chemistry, 2000, DOI: 10.1002/14356007.a24_001).

A similar approach is followed in the teaching of EP 1 381 589 B1. Zeolite materials are post-treated with phosphoric as well as boric acid. The catalysts thus obtained reveal a certain activity in MDA synthesis. The ratio of 4,4'-MDA to 2,4'-MDA was increased from 2.2 to a maximum of 6.95.

EP-A-0 264 744 describes the condensation of aniline with trioxane or free formaldehyde and the rearrangement to MDA using solid boron, titanium and iron-containing zeolites. Simultaneous condensation and rearrangement as well as isolation of aminobenzylanilines with subsequent rearrangement to MDA are both disclosed. Although high monomer selectivity was obtained by rearrangement of the intermediate aminobenzyl anilines to MDA (approx. 90 mol % MMDA in the product after removal of aniline), complete conversion is not achieved. Furthermore the reaction is preferably performed in an additional solvent which is undesirable from an economic perspective.

WO/0158847 A1 describes a process for the production of MDA containing high amounts of MMDA with low ortho-content via a solid acid-catalysed rearrangement of a condensation product from aniline and formaldehyde or another methylene group-supplying agent like trioxane or para-formaldehyde. Preferred solid catalysts are FAU zeolites. The invention is directed at a process which produces an MDA with as little PMDA as possible. However, whilst very high monomer contents might be desirable for certain special applications, it is not desired as a rule in industry to avoid the formation of PMDA since the latter has proven to be useful in many applications. In addition, the process requires the use of highly pure aniline with a very low content of aliphatic amines.

Zeolitic materials based on faujasite structure were utilized as catalysts in MDA synthesis according to method described in CZ 0 301 977 B6. High yields of monomeric MDA were obtained, whereas an A/F of 10 was applied. The recipe makes the industrial process economically unattractive since excess aniline has to be removed from the MDA if it is later on utilized as precursor for MDI.

Exchange of the protic sites in zeolites by alkaline metals is described in JP 2012 131720 A. Lithium-modified faujasite-type zeolites show activity in the rearrangement towards MDA. However, the conversion of the intermediate aminobenzylanilines to MDA is incomplete.

The solid acid catalysed MDA synthesis is reported in JP 2012 250971 A. Silica-alumina and Y zeolites are described as solid catalysts. However, the conversion of the intermediate aminobenzylanilines to MDA is incomplete.

EP-A-0 329 367 describes the rearrangement of a dried aminal over metal-containing zeolitic catalysts for the purpose of selectively producing MMDA. The aminal is rearranged isothermally at 120° C. using steam-dealuminated HY zeolites and fluorinated derivatives thereof to give a MDA, which although consisting of approx. 94 mol % (relative to aniline-free solution) of MMDA is characterized by incomplete conversion of the intermediates to the MDA. Approximately 5 mol % of PMDA are additionally formed.

Concerning steam-dealuminated HY zeolites, mechanistic studies for aminal rearrangement can be found in Michael Salzinger et al., Green Chem., 2011, 13, 149-155. Based on kinetic time profiles, it is concluded in this reference that the reaction order of the first step (rearrangement of the aminal to yield aminobenzylanilines) is one, whereas that of the second step (rearrangement of aminobenzylanilines to MDA) is two. Moreover, this study reveals either film or pore diffusion limitations especially for the first step, leading to decreased turnover at the active sites and negatively affecting the space-time-yield of the overall process.

Through delamination of layered, template-containing zeolite precursors through swelling agents and ultrasound, the acid sites can be made accessible to bulkier molecules, and diffusion limitations avoided (Pablo Botella et al., Appl. Catal., A, 2011, 398, 143-149, WO 03/082803 A1). The catalytic activity of these zeolites with respect to aminal conversion employing a molar ratio of aniline to formaldehyde (hereinafter "A/F") of 3 is described. The MDA thus obtained contains approximately 25% of PMDA. The exfoliation process results in reduced acid strength compared to zeolitic materials (cf. Avelino Corma et al., Microporous Mesoporous Mater., 2000, 38, 301-309) and thus in a low 4,4'-MDA/2,4'-MDA ratio. Furthermore, this approach is limited to layered zeolites, whose synthesis relies on the application of sacrificial templates and surfactants. The relatively high cost of the zeolites, combined with the excessive consumption of surfactants in the delamination process, render an industrialization of this approach unattractive.

Desilication by alkaline treatment enables to generate mesopores in zeolites while increasing the aluminium content (Javier Pérez-Ramírez et al., Chem. Soc. Rev., 2008, 37, 2530-2542). Mesoporous zeolites thus produced have been tested in various catalytic reactions (liquid-phase degradation of high density polyethylene, cumene cracking, oligomerisation of styrene, liquid-phase benzene alkylation, butane aromatisation, conversion of methanol to gasoline and methanol to propylene, ion-exchange and redox catalysis).

Martin Spangsberg et al., Catal. Today, 2011, 168, 3-16 discloses examples of the successful utilization of hierarchical zeolites, i.e. zeolites which have been subjected to a defined post-synthetic design process so as to result in zeolitic structures featuring at least one additional level of porosity besides the intrinsic micropore system characteristic of zeolites, in various acid- and base-catalysed reactions of scientific and industrial relevance. The reference mentions alkylation reactions, methanol to hydrocarbon and aromatization reactions, isomerization reactions of hydrocarbons, cracking reactions, condensation reactions such as aldol condensations, esterification reactions, acetalisation reactions, and other reactions such as the Beckmann rearrangement, epoxidation and hydroxylation reactions, hydrotreating reactions and the decomposition of nitrogen oxides. No reference is made to MDA synthesis.

Danny Verboekend et al., *Catal. Sci. Technol.*, 2011, 1, 879-890 and Danny Verboekend et al., *Chem. Mater.*, 2013, 25, 1947-1959 describe various post-synthetic strategies to obtain hierarchical zeolites. These strategies have evolved far beyond the point of conventional desilication. The catalytic and adsorptive properties of the hierarchical zeolites are evaluated in the Chem. Mater. reference, disclosing their use in the alkylation of toluene with benzyl alcohol or isopropyl alcohol and the Knoevenagel condensation of benzaldehyde with malonitrile. The use of hierarchical clinoptilotite in alkylations is envisaged. The Catalysis Science & Technology reference discloses the use of hierarchical zeolites in a wide range of reactions mentioning isomerisation, alkylation, acylation, aromatisation, cracking, pyrolysis, methanol-to-hydrocarbons conversions, gas-oil hydrocracking, pyrolysis of low-density polypropylene and biocatalysis. MDA synthesis is not mentioned in any reference.

The use of a BEA (=beta) zeolite which was alkaline-treated in the absence of a pore-directing agent in MDA synthesis is disclosed in Michael Salzinger et al., *Appl. Catal., A*, 2011, 393, 189-194. The reference explicitly discourages the skilled person to use alkaline treatment, be it in the presence or absence of a pore-directing agent, for zeolites other than BEA zeolites (see page 193, right column, second paragraph) due to the destruction of the zeolite framework. The parent zeolite is first treated with NaOH and then with $NH_4Cl$ (so as to replace sodium by ammonium). Even for the beta zeolite, the authors report show that already after 15 min of alkaline leaching, the BEA framework is severely damaged based on XRD diffractograms.

A regeneration process of beta zeolite having been employed in MDA production is described in EP 1 294 481 B1 by interrupting the feed of aminal and feeding aniline (as regenerating agent) instead. In addition, the initial temperature was raised from 180° C. to 250° C. Before and after regeneration, the catalysts exhibited the same characteristics with regard to isomer as well as polymer composition.

Attempts have also been made to perform the rearrangement of aminal via aminobenzyl aniline to MDA in several steps, for example in two steps, using solid acids in more than one step. U.S. Pat. No. 4,039,581 describes the rearrangement of the aminal using solid acids, whereby the aminal is first dried and then rearranged using zeolites, for example, in several reaction stages with increasing temperature. A temperature of 100° C. is not exceeded. It is assumed that high temperatures in the presence of water would be damaging to selectivity. A full rearrangement of the aminobenzyl aniline intermediates to the MDA cannot be achieved under these conditions. MDA with an MMDA content of approx. 90 mol % in the aniline-free mixture is obtained as product.

WO 2010/072504 A1 describes a continuous process for the synthesis of MDA using solid catalysts. Besides others, different types of silica-alumina as well as clays serve in the first stage to convert aminal towards intermediates like aminobenzylanilines. In the second stage, MMDA and higher homologues are obtained by treating the intermediate mixture with solid catalysts like zeolites, delaminated zeolites or ordered mesoporous materials. The yield of monomeric MDA decreased in general by increasing run-time depending on the choice of catalyst. The necessity of using two different types of catalysts renders the process undesirably complicated.

To summarise, there has been considerable progress in the area of solid zeolite catalysis for MDA synthesis. However, up to now no process is known which really has the potential to replace traditional HCl catalysis on a large industrial scale. Therefore, there still exists a need to improve solid zeolite catalysis in MDA synthesis. The present invention addresses this need.

SUMMARY OF THE INVENTION

Therefore, the present invention provides a process for the preparation of di- and polyamines of the diphenylmethane series by the rearrangement of a condensation product of aniline and a methylene group-supplying agent, wherein said condensation product is reacted in the presence of at least one solid zeolite catalyst partially or fully ion-exchanged to the protonic form which has been
A) alkaline-treated, wherein the alkaline treatment is in case of BEA zeolites carried out in the presence of a pore-directing agent and in case of zeolites other than BEA zeolites in the presence or absence of a pore-directing agent,
or
B) acid-treated without any alkaline treatment preceding or following said acid treatment, wherein the acid treatment is effected with an organic acid with chelating function.

The alkaline treatment A) can be preceded and/or followed by any other treatment (e.g. an acid treatment or another alkaline treatment). The acid treatment B) can be preceded and/or followed by any other treatment other than an alkaline treatment.

DETAILED DESCRIPTION

Without wishing to be bound by a theory, it is believed that these treatments aim to generate external surface area in the zeolite crystals while preserving the active site properties. This should lead to increased utilization of the catalyst volume, while the characteristic performance of a zeolite, i.e. the obtained 4,4'-MDA/2,4'-MDA ratio is retained.

In particular, preferred zeolites A) used according to the process of the invention are selected from the group consisting of:
(i) zeolites other than BEA zeolites which have been alkaline-treated in the presence or absence of a pore-directing agent;
(ii) BEA zeolites which have been alkaline-treated in the presence of a pore-directing agent;
(iii) zeolites which have been acid-treated in a first step and alkaline-treated in a second step;
(iv) zeolites which have been alkaline-treated in a first step and acid-treated in a second step;
(v) zeolites which have been acid-treated in a first step, alkaline treated in a second step and acid-treated in a third step;
and
(vi) mixtures thereof;
wherein any acid-treatment step is preferably affected by an organic acid with chelating function.

Methylene group-supplying agents which can be used in the process for the preparation of di- and polyamines of the diphenylmethane series according to the invention include aqueous formaldehyde solution, gaseous formaldehyde, para-formaldehyde, trioxane and mixtures thereof. Aqueous formaldehyde solution is particularly preferred. For the process of the present invention, preferably aqueous formaldehyde of technical quality having a formaldehyde concentration of 30% by weight to 50% by weight is used; typically this technical formaldehyde solution contains methanol in a 0.1% by weight to 15% by weight range. It is also possible to use aqueous formaldehyde solutions which have a lower or a higher formaldehyde concentration than mentioned before.

For the process according to the invention, aniline grades are preferably used that are largely free from aliphatic amines as minor and trace constituents (e.g. cyclohexylamine, dicyclohexylamine). For the process according to the invention, aniline with a purity of ≥99.5% is preferably used. In this context, the purity of the aniline refers to the purity of aniline freshly introduced into the process from an outside source ("fresh aniline"). As is well known in the art, the aniline which, in a process on an industrial scale, is actually reacted with the methylene group-supplying agent is usually a mixture of such "fresh aniline" and aniline streams which have been recycled from other parts of the process, the latter usually being less pure.

In the context of the present invention, the expression "organic acids with chelating function" refers to organic Brønsted acids with at least two acidic sites in their protonated or deprotonated (i.e. as salt) form. Preferably, the acid is chosen from the group consisting of ethylene diamine tetra acetic acid (EDTA), citric acid, oxalic acid and mixtures thereof. Such acids are capable of leaching aluminium from the zeolite. Preferably, acids are chosen which are capable of leaching at least 5% of the aluminium present in total in the zeolite, as determined by ICP-OES, if 10 g $L^{-1}$ of the zeolite are subjected to a treatment of a 0.1 M aqueous solution of the acid at a temperature of 100° C. for 6 hours. The respective method has been described by W. Zamechek in *Verified Synthesis of Zeolithic Materials* (Eds: H. Robson, K. P. Lillerud), 2nd Ed., Elsevier, 2001, pp. 51-53.

The process according to the invention is preferably performed in the absence of solvents.

In a preferred embodiment of the invention, the methylene group-supplying agent is reacted with aniline in the absence of an acidic catalyst, whereby a (condensation) product is formed that can be given the alternative name of aminal and consists predominantly of N,N'-diphenyl-methylenediamine. This condensation product is preferably separated from the water of reaction when using aqueous formaldehyde solution, gaseous formaldehyde or mixtures thereof with the other methylene group-supplying agents mentioned before by phase separation and may further be dehydrated before the further reaction is performed under catalysis, although such an additional dehydration step is not strictly necessary and can be dispensed with.

In principle, the reaction of aniline and the methylene group-supplying agent to give the aminal can be performed also in the presence of a catalyst that causes the rearrangement to aminobenzylaniline (ABA) and/or the MDA isomers. However, the water that is released during the condensation reaction when using aqueous formaldehyde solution, gaseous formaldehyde or mixtures thereof with the other methylene group-supplying agents mentioned before reduces the activity and selectivity of the catalyst, as a consequence of which the successive version (aminal reaction→phase separation→rearrangement) is preferred.

The aminal reaction is preferably performed continuously by metering aniline and formaldehyde solution in a molar ratio of aniline to formaldehyde of 1.7 to 100, preferably 1.8 to 50, particularly preferably 2 to 20, into a reactor, from which a reaction quantity of the same volume as the feed stream is continuously removed and sent for phase separation. A batchwise or semi-continuous process is also conceivable, whereby the aniline and formaldehyde are metered in the desired mixing ratio into a stirred batch reactor, from which the aminal that is reacted out is then sent for drying.

The desired molar ratio of aniline to formaldehyde (A/F) for the rearrangement can be set at the time of the aminal reaction, optionally taking the drying losses into consideration. In principle, however, it is also possible to perform the aminal reaction at a lower molar A/F as desired and then to set the desired value immediately before the rearrangement using pure, dry aniline. The latter option allows the use of smaller apparatus at the aminal reaction and drying stages, leading to lower investment costs. Aniline recovered from reprocessing of the reaction mixture (recycled aniline) can also be used for restocking after condensation, which in the case of the operation using an excess of aniline is recovered from the fully rearranged MDA.

The rearrangement can preferably be performed batchwise or continuously in a stirred-tank reactor, a series of stirred-tank reactors, in a tubular reactor (e.g. fixed-bed or fluidised-bed reactor) or in a combination thereof. Serial fixed catalyst beds are advantageously used. A mixture of aminobenzylanilines, aniline and small quantities of diaminophenylmethanes is preferably first obtained in a temperature range of 20° C. to 70° C., particularly preferably 40° C. to 60° C., depending on the catalyst used. To this end, the reaction mixture is preferably pumped over the fixed catalyst bed, whereby residence times of 0.2 to 2 hours are typically set. The optimum temperature for a selected catalyst and a desired isomer ratio in the aminobenzyl-anilines obtained is easily determined by means of preliminary tests.

The reaction to MDA is completed using the same or another catalyst bed at an increased temperature of 70° C. to 200° C., particularly preferably of 70° C. to 160° C., whereby residence times of 0.2 to 48 hours, preferably 0.5 to 24 hours, particularly preferably 1 to 18 hours are typically set. The phrase "another catalyst bed" can describe either another catalyst bed having the same composition than the first catalyst bed, or another catalyst bed based on a different catalyst composition than the first catalyst bed or a combination thereof.

On completion of the reaction, the reaction mixture obtained by the process according to the invention and after separation from the catalyst can be processed such that the excess aniline optionally contained in the mixture can be separated from the MDA isomers either continuously or batchwise by known methods such as distillation or crystallisation, for example, and recycled. The MDA isomers are then preferably sent for subsequent phosgenation.

The solid zeolite catalysts used according to the invention can be referred to as "hierarchical zeolites", i.e. zeolites which have been subjected to a defined post-synthetic design process (such as the treatments (i) to (v) referred to above) so as to result in zeolitic structures featuring at least one additional level of porosity besides the intrinsic micropore system characteristic of zeolites, as described in *Catal. Today*, 2011, 168, 3-16.

The solid zeolite catalysts used according to the invention can be prepared from any known zeolite. The starting material zeolite, i.e. a zeolite which has not yet been subjected to a post-synthetic design process as described above (in the following also referred to as parent zeolite), can be chosen from any zeolite known in the art, that needs to be partially or fully detemplated in case an organic template was used during its hydrothermal synthesis. The parent zeolite may have been subjected to treatments other than the ones described in A) or B), including but not limited to calcination, ion-exchange, steaming and acid treatments with mineral acids. Preference is given to 3D-frameworks with 12 membered-ring pore openings such as FAU and BEA, especially FAU (faujasite).

The acid treatment of zeolite type B) is preferably carried out by contacting the zeolite with aqueous solutions of organic acids with chelating character such as ethylene diamine tetra acetic acid (EDTA), citric acid, oxalic acid or mixtures thereof in a temperature range of from 10° C. to 100° C., a concentration range of from 0.01 mol L$^{-1}$ to 1 mol L$^{-1}$ for a period of from 0.25 hours to 100 hours. A semi-batch wise addition of the acids to the solution is preferred.

The alkaline treatment of zeolite type A) (i) is preferably carried out in a pH range of 10 to 15, preferably 11 to 14, using alkali metal hydroxide solutions, preferably NaOH and/or KOH. Also ammonia or basic salts are feasible. Typical treatment conditions comprise contacting the zeolite with the basic solution in batch, semi-batch or continuous mode in a temperature range of from 10° C. to 100° C. for a period of from 0.1 minutes to 180 minutes with a zeolite loading of 5 g L$^{-1}$ to 400 g L$^{-1}$, "L" referring to the volume of the total reaction mixture. According to the invention, this alkaline treatment may take place in the presence of a pore-directing agent. These serve to stabilize the zeolite in the alkaline environment and prevent the amorphization of the crystalline framework. Suitable pore-directing agents are alkylammonium cations with the general molecular formula $^+NR^i_4$, wherein the four $R^i$ substituents $R^1, R^2, R^3$ and $R^4$ can be the same or different and can be organic substituents or hydrogen. In particular, the four $R^i$ substituents can be any combination of branched/linear alkanes, alkenes, aromatics hydrocarbons and protons, with preference being given to $R^i$=linear alkyl substituents with 1-3 carbon atoms. The counter ion X$^-$ of the alkylammonium cation is preferably chosen from the group consisting of hydroxides, halides, sulphates, nitrates and alkoxydes, whereof hydroxides, chlorides, bromides and methanolates are preferred.

The alkaline treatment of zeolite type A) (ii) is preferably carried out as described above for type (i) with the exception that the use of a pore-directing agent is mandatory.

The acid treatment of zeolite type A) (iii) is preferably carried out as described above for zeolite type B), however, a chelating character is not mandatory for the acid employed. Accordingly, in addition to the acids mentioned above, mineral acids such as hydrochloric acid, nitric acid phosphoric acid are also applicable.

This acid treatment is followed by an alkaline treatment, which is preferably carried out as described above for zeolite type (i). It is preferred to carry out this alkaline treatment in the absence of a pore-directing agent.

The alkaline treatment and acid treatment of zeolite type A) (iv) is preferably carried out as described for zeolite type (iii) with the order of treatment steps being reversed.

The acid treatment steps of zeolite type A) (v) are preferably carried out as described for zeolite type A) (iii). The alkaline treatment step between the two acid treatment steps is preferably carried out as described for zeolite type (i). It is preferred to carry out this alkaline treatment in the absence of a pore-directing agent.

Furthermore, it is preferred that the respective treatment A) or B) is performed such that the zeolite obtained after completion of the respective treatment has a crystallinity as determined by X-ray diffraction analysis of at least 50% when compared to the parent zeolite before the respective treatment A) or B). Quantification of crystallinity by X-ray diffraction should be carried out according to the ASTM standard issued under the jurisdiction of D32.05 or equivalent methods with the ASTM standard being the prevailing method in case of any discrepancy.

These solid zeolite catalysts can in principle be used both in powder form and in lump form, whereby the conventional industrial processes of tabletting, pelletising or extrusion, for example, can be used for moulding, optionally with the aid of moulding additives such as binders, porogens, lubricants, plasticisers and fillers, as further detailed in Sharon Mitchell et al., *Chem. Soc. Rev.*, 2013, 42, 6094-6112. For industrial use in the continuous process, the catalyst is preferably used after moulding to run solid catalyst beds. In batch-wise operation the catalysts are preferably used in quantities of 0.1 wt. % to 50 wt. % relative to the reaction mixture, in continuous operation preferably in quantities of 0.01 kg to 100 kg aminal/(kg catalyst·h), especially preferably in quantities of 0.025 kg to 40 kg aminal/(kg catalyst·h). Different grades and geometries, etc. of catalysts can also be used during the course of the process.

EXAMPLES

I. Preparation of Aminal

I.1 Aminal "A" from Aniline/Formaldehyde Ratio of 3

In a four-neck round-bottom flask charged with nitrogen, 150 g aniline were added and heated under stirring to a temperature of 80° C. Then, a further portion of 315.7 g aniline as well as 134 g of aqueous formaldehyde solution (37.1 wt.-% HCHO) were added dropwise via separate dropping funnels within 20 minutes. The suspension thus obtained was further stirred for 10 minutes and in the next step transferred to an evacuated separation funnel, in which the suspension was allowed to settle for 20 minutes. The aqueous phase was separated from the aminal phase, whereby the latter one was used as starting material for the catalytic runs described in the following examples.

I.2 Aminal "B" from Aniline/Formaldehyde Ratio of 2.5

The preparation was conducted in the same fashion compared to I.1 with the exception of applying 161.9 g formaldehyde solution (37.1 wt.-% HCHO).

I.3 Aminal "C" from Aniline/Formaldehyde Ratio of 2

The preparation was conducted in the same fashion compared to I.1 with the exception of applying 202.4 g formaldehyde solution (37.1 wt.-% HCHO).

II. Preparation of Zeolite Catalysts

Zeolites whose preparation is not described in the following were purchased from commercial sources and used as obtained.

Modified zeolite catalysts were prepared from commercially available zeolites as listed in Table 1. Treatments were carried out in stirred glass reactors. After the treatments, zeolites were filtered off and washed three times with 1 L of deionized water. Lastly, all the zeolites were ion-exchanged to the ammonium form by suspending 10 g L$^{-1}$ of zeolite in a 0.1 M ammonium nitrate solution at room temperature for 8 hours. This procedure was repeated three times. The obtained solids were dried at 65° C. and heated to 550° C. for 5 h with a ramp rate of 5° C. min$^{-1}$ to obtain the protonic form of the zeolites.

TABLE 1

Overview of synthesized catalysts.

| Code | Catalyst | Parent Zeolite | Step | Reactants | Temperature | Time |
|---|---|---|---|---|---|---|
| II.1 | FAU6-ATN0.15 | Zeolyst CBV712 | 1 | 6.6 g of zeolite, 1.2 g of NaOH, 200 g of water | 65° C. | 0.5 h |
| II.2 | FAU6-ATN0.20 | Zeolyst CBV712 | 1 | 6.6 g of zeolite, 1.6 g of NaOH, 200 g of water | 65° C. | 0.5 h |
| II.3 | FAU6-ATAW | Zeolyst CBV712 | 1 | 6.6 g of zeolite, 1.6 g of NaOH, 200 g of water | 65° C. | 0.5 h |
|  |  |  | 2 | 4 g of zeolite from step 1, 2.48 g of NaOH, 60 g of water | 100° C. | 6 h |
| II.4 | FAU15-AT0.05 | Zeolyst CBV720 | 1 | 6.6 g of zeolite, 0.4 g of NaOH, 10.65 g of tetrapropylammonium bromide, 200 g of water | 65° C. | 0.5 h |
| II.5 | FAU15-AT0.10 | Zeolyst CBV720 | 1 | 6.6 g of zeolite, 0.8 g of NaOH, 10.65 g of tetrapropylammonium bromide, 200 g of water | 65° C. | 0.5 h |
| II.6 | FAU15-AT0.15 | Zeolyst CBV720 | 1 | 6.6 g of zeolite, 1.2 g of NaOH, 10.65 g of tetrapropylammonium bromide, 200 g of water | 65° C. | 0.5 h |
| II.7 | FAU15-AT0.20 | Zeolyst CBV720 | 1 | 6.6 g of zeolite, 1.6 g of NaOH, 10.65 g of tetrapropylammonium bromide, 200 g of water | 65° C. | 0.5 h |
| II.8 | FAU15-AT0.25 | Zeolyst CBV720 | 1 | 6.6 g of zeolite, 2.0 g of NaOH, 10.65 g of tetrapropylammonium bromide, 200 g of water | 65° C. | 0.5 h |
| II.9 | FAU15-AT0.30 | Zeolyst CBV720 | 1 | 6.6 g of zeolite, 2.4 g of NaOH, 10.65 g of tetrapropylammonium bromide, 200 g of water | 65° C. | 0.5 h |
| II.10 | FAU15-AT0.45 | Zeolyst CBV720 | 1 | 6.6 g of zeolite, 3.6 g of NaOH, 10.65 g of tetrapropylammonium bromide, 200 g of water | 65° C. | 0.5 h |
| II.11 | FAU15-ATN0.20 | Zeolyst CBV720 | 1 | 6.6 g of zeolite, 1.6 g of NaOH, 200 g of water | 65° C. | 0.5 h |
| II.12 | FAU30-AT0.15 | Zeolyst CBV760 | 1 | 6.6 g of zeolite, 1.2 g of NaOH, 10.65 g of tetrapropylammonium bromide, 200 g of water | 65° C. | 0.5 h |
| II.13 | FAU40-AT0.05 | Zeolyst CBV780 | 1 | 6.6 g of zeolite, 0.4 g of NaOH, 10.65 g of tetrapropylammonium bromide, 200 g of water | 65° C. | 0.5 h |
| II.14 | FAU385-AT0.20 | Tosoh HSZ-390HUA | 1 | 6.6 g of zeolite, 1.6 g of NaOH, 10.65 g of tetrapropylammonium bromide, 200 g of water | 65° C. | 0.5 h |
| II.15 | BEA20-AT0.15 | Tosoh HSZ-940HOA | 1 | 6.6 g of zeolite, 1.2 g of NaOH, 10.65 g of tetrapropylammonium bromide, 200 g of water | 65° C. | 0.5 h |
| II.16 | BEA220-AT0.15 | Tosoh HSZ-980HOA | 1 | 6.6 g of zeolite, 1.2 g of NaOH, 10.65 g of tetrapropylammonium bromide, 200 g of water | 65° C. | 0.5 h |
| II.17 | MFI15-ATAW | Zeolyst CBV3024E | 1 | 6.6 g of zeolite, 4.8 g of NaOH, 200 g of water | 65° C. | 0.5 h |
|  |  |  | 2 | 3 g of zeolite from step 1, 2.05 g of HCl (35% in water), 298 g of water | 65° C. | 6 h |
| II.18 | MFI25-ATN0.30 | Zeolyst CBV5524G | 1 | 6.6 g of zeolite, 2.4 g of NaOH, 200 g of water | 65° C. | 0.5 h |
| II.19 | MFI40-ATN0.20 | Zeolyst CBV8014 | 1 | 6.6 g of zeolite, 1.6 g of NaOH, 200 g of water | 65° C. | 0.5 h |
| II.20 | MFI140-AT0.20 | Zeolyst CBV28014 | 1 | 6.6 g of zeolite, 1.6 g of NaOH, 10.65 g of tetrapropylammonium bromide, 200 g of water | 65° C. | 0.5 h |
| II.21 | MFI1000-AT0.20 | Tosoh HSZ-890HOA | 1 | 6.6 g of zeolite, 1.6 g of NaOH, 10.65 g of tetrapropylammonium bromide, 200 g of water | 65° C. | 0.5 h |
| II.22 | MOR10-DAAT | Zeolyst CBV21A | 1 | 10 g of zeolite, 13.53 g HNO$_3$ (65% in water), 87 g of water | 100° C. | 1 h |
|  |  |  | 2 | 6.6 g of zeolite, 1.2 g of NaOH, 200 g of water | 65° C. | 0.5 h |
| II.23 | HEU5-DAAT | KMI Zeolite Clinoptilolite | 1 | 12 g of zeolite, 12.45 g HCl (35% in water), 170 g of water | 100° C. | 1 h |
|  |  |  | 2 | 10 g of zeolite, 10.38 g HCl (35% in water), 142 g of water | 100° C. | 1 h |
|  |  |  | 3 | 8 g of zeolite, 8.30 g HCl (35% in water), 113 g of water | 100° C. | 1 h |
|  |  |  | 4 | 6 g of zeolite, 6.23 g HCl (35% in water), 85 g of water | 100° C. | 1 h |
|  |  |  | 5 | 4 g of zeolite, 0.97 g of NaOH, 121 g of water | 65° C. | 1 h |

II.24 Preparation Procedure for MCM-41 (Comparative Example)

0.612 g NaAlO$_2$ were dissolved in 600 g H$_2$O and 12 g of cetyltrimethylammoniumbromide were added. The suspension was stirred at 60° C. until complete dissolution occurred and cooled to room temperature before adding 45 g NH$_4$OH (56 wt. % in H$_2$O) and 46.7 g tetraethylorthosilicate. The precipitated solid was filtered after stirring for 1 h at room temperature and washed with deionized water. The filter cake was dried at 65° C. and heated to 550° C. for 10 hours under air flow with a ramp rate of 2° C. min$^{-1}$. The solid thus obtained was suspended in a solution of 2.64 g NH$_4$NO$_3$ in 330 g H$_2$O for 8 h at room temperature. This procedure was repeated three times. The material thus obtained was dried at 65° C. and heated to 550° C. for 5 h with a ramp rate of 5° C. min$^{-1}$ to obtain MCM-41.

II.25 Preparation Procedure for ITQ-2 Zeolites (Comparative Example)

All materials were synthesized according to reported preparations (ZSM-22(P) synthesis according to A. Corma in *Verified Syntheses of Zeolitic Materials* (Eds: H. Robson and K. P. Lillerud), 2. Edition, Elsevier, 2001, pp. 225-227. Delamination procedure according to M. Salzinger, M. B. Fichtl, J. A. Lercher, *Appl. Catal., A* 2011, 393, 189-194.).

For the synthesis of ITQ-2, the parent zeolite (ZSM-22) had to be prepared first. For this purpose, 248.4 g of water was mixed with 1.84 g sodium aluminate and 1.2 g of sodium hydroxide. 15.22 g hexamethyleneimine was added and the solution mixed throughly before 18.46 g of fumed silica was added portion wise. The obtained thick gel was transferred into an autoclave and incubated in a rotary oven at 150° C. and 60 rpm for 7 days. The catalyst was filtered off and washed with deionized water to obtain MCM-22(P)

5.4 g of MCM-22(P) were suspended in 99.5 g of H$_2$O, 66.5 g of tetrapropylammonium hydroxide solution (20 wt. %) and 7.67 g of hexadecyltrimethylammonium bromide at 80° C. for 16 hours and introduced into an ultrasonic bath for 1 hour. Through addition of concentrated HCl, the pH was reduced to 2 and the solution filtered off. The obtained material was dried in static air at 100° C. and calcined at 550° C. for for 8 hours with a ramp rate of 2° C. min$^{-1}$. The obtained solid was suspended in a solution of 2.64 g NH$_4$NO$_3$ in 330 g H$_2$O for 8 h at room temperature. This procedure was repeated three times, before calcination at 550° C. for 5 h with a ramp rate of 5° C. min$^{-1}$. The yield was 3.4 g.

III. Catalytic Tests

For running the catalytic experiments, a multi-batch reactor system (AMTEC, SPR-16) was used consisting of 16 parallel reactors with a volume of 15 mL each. Each reactor was pressurized with nitrogen, filled with the respective zeolite (0.1 to 1 g) and aminal (4.9 g, prepared as described under A). Agitation was achieved via magnetic stirring at 500 rpm and the system was heated up to a temperature of 140° C. After a reaction time that varied between 1 and 4 hours—in some cases 24 h—, the reactors were cooled to room temperature. The suspension was filtered through a syringe filter and an aliquot from the filtrate was taken for HPLC analysis (Agilent 1100 Series), for which a mixture of methanol, water and acetonitrile was used as eluent and a phenomenex column as stationary phase. Applying a method with external 3-point calibration, the components mentioned in the next examples could be quantified. Prior to injection, the respective aliquot (approximately 50 mg) was diluted in an N-ethyldiisopropylamine solution of 50 mL (0.12% w/w in methanol/THF solution (1:2 w/w)) and transferred in a vial. For comparability, excess aniline was subtracted in the quantities given in the tables below.

III.1 Examples 1 to 14 (Catalytic Runs with Faujasite and Beta Zeolites and Modifications Thereof)

For the experiments in examples 1 to 14, aminal "A" was used, the catalyst amount was 0.1 g and the reaction time 4 h resulting in a load of 12.25 $g_{Aminal}/(g_{Catalyst} \cdot h)$.

TABLE 2

Overview of catalytic runs 1 to 14.

| III.1 | Code[1] | ABAs[2] % | MMDA[3] % | PMDA[4] % | Others[5] % | 4,4'-MDA/ 2,4'-MDA |
|---|---|---|---|---|---|---|
| 1 | II.3 | 13.8 | 58.4 | 8.4 | 19.5 | 6.0 |
| 2 | FAU6 | 45.7 | 20.8 | 0.7 | 32.8 | 6.0 |
| 3 | II.7 | 8.2 | 69.5 | 7.3 | 15.0 | 6.6 |
| 4 | FAU15 | 29.4 | 40.9 | 2.0 | 27.7 | 6.5 |
| 5 | II.12 | 27.2 | 42.3 | 3.8 | 26.7 | 6.1 |
| 6 | FAU30 | 30.2 | 38.9 | 1.9 | 29.0 | 6.0 |
| 7 | II.13 | 31.5 | 37.8 | 2.1 | 28.7 | 5.5 |
| 8 | FAU40 | 42.6 | 23.9 | 0.9 | 32.6 | 5.3 |
| 9 | II.14 | 57.4 | 10.0 | 0.5 | 32.1 | 5.9 |
| 10 | FAU385 | 58.9 | 2.4 | 0.0 | 38.7 | 5.3 |
| 11 | II.15 | 4.0 | 69.9 | 10.8 | 15.3 | 2.9 |
| 12 | BEA20 | 50.5 | 14.9 | 0.4 | 34.3 | 2.2 |
| 13 | II.16 | 48.4 | 18.0 | 0.6 | 33.1 | 1.5 |
| 14 | BEA220 | 54.7 | 7.8 | 0.2 | 37.3 | 1.9 |

[1]Code refers to Chapter II, parent zeolite for reference without treatment,
[2]o- and p-ABA,
[3]4,4'-, 2,4'-, 2,2'-, 4,4'-N-Formyl- and 4,4'-N-Methyl-MDA,
[4]3- and 4-ring isomers,
[5]5-ring and non identifiable products.

Under the same reaction conditions, the modified catalysts revealed a higher content of MMDA compared to the parent samples without treatment. The space-time yield of MMDA is therefore increased.

III.2 Examples 15 to 28 (Catalytic Runs with Heulandite, Mordenite, ZSM-5 and Modifications Thereof)

For the experiments in examples 15 to 28, aminal "A" was used, the catalyst amount was 0.1 g and the reaction time 4 h resulting in a load of 12.25 $g_{Aminal}/(g_{Catalyst} \cdot h)$.

TABLE 3

Overview of catalytic runs 15 to 28

| III.2 | Code[1] | ABAs[2] % | MMDA[3] % | PMDA[4] % | Others[5] % | 4,4'-MDA/ 2,4'-MDA |
|---|---|---|---|---|---|---|
| 15 | II.23 | 47.0 | 16.8 | 1.3 | 34.9 | 5.0 |
| 16 | HEU5 | 61.9 | 2.7 | 0.0 | 35.4 | 4.9 |
| 17 | II.17 | 59.0 | 10.8 | 1.0 | 29.2 | 4.0 |
| 18 | MFI15 | 58.1 | 5.7 | 0.2 | 36.0 | 3.5 |
| 19 | II.18 | 20.7 | 48.1 | 6.2 | 25.0 | 4.7 |
| 20 | MFI25 | 60.7 | 3.7 | 0.1 | 35.6 | 3.0 |
| 21 | II.19 | 15.6 | 54.4 | 8.0 | 22.0 | 4.0 |
| 22 | MFI40 | 54.0 | 10.2 | 0.2 | 35.5 | 4.1 |
| 23 | II.20 | 59.5 | 5.1 | 0.1 | 35.3 | 3.0 |
| 24 | MFI140 | 63.0 | 0.6 | 0.0 | 36.5 | 2.8 |
| 25 | II.21 | 60.8 | 0.2 | 0.0 | 39.1 | — |
| 26 | MFI1000 | 52.6 | 0.1 | 0.0 | 47.3 | — |
| 27 | II.22 | 54.3 | 11.7 | 0.2 | 33.9 | 6.0 |
| 28 | MOR10 | 63.3 | 2.2 | 0.1 | 34.4 | 3.2 |

[1]Code refers to Chapter II, parent zeolite for reference without treatment,
[2]o- and p-ABA,
[3]4,4'-, 2,4'-, 2,2'-, 4,4'-N-Formyl- and 4,4'-N-Methyl-MDA,
[4]3- and 4-ring isomers,
[5]5-ring and non identifiable products.

Under the same reaction conditions, the modified catalysts revealed a higher content of MMDA compared to the parent samples without treatment. The space-time yield of MMDA is therefore increased.

III.3 Examples 29 to 35 (Catalytic Runs with Faujasite-15 and Modifications Thereof)

For the experiments in examples 29 to 35, aminal "A" was used, the catalyst amount was 0.1 g and the reaction time 1 h resulting in a load of 49.00 $g_{Aminal}/(g_{Catalyst} \cdot h)$.

TABLE 4

Overview of catalytic runs 29 to 35.

| III.3 | Code[1] | ABAs[2] % | MMDA[3] % | PMDA[4] % | Others[5] % | 4,4'-MDA/ 2,4'-MDA |
|---|---|---|---|---|---|---|
| 29 | FAU15 | 37.9 | 30.1 | 1.0 | 31.0 | 6.6 |
| 30 | II.4 | 26.9 | 44.1 | 2.3 | 26.8 | 6.8 |
| 31 | II.5 | 26.6 | 44.2 | 2.3 | 26.9 | 6.9 |
| 32 | II.6 | 22.7 | 48.7 | 2.9 | 25.6 | 7.1 |
| 33 | II.7 | 15.3 | 60.1 | 4.9 | 19.7 | 7.1 |
| 34 | II.8 | 13.0 | 63.3 | 5.5 | 18.2 | 7.1 |
| 35 | II.9 | 11.1 | 66.2 | 6.2 | 16.5 | 7.1 |

[1]Code refers to Chapter II, parent zeolite for reference without treatment,
[2]o- and p-ABA,
[3]4,4'-, 2,4'-, 2,2'-, 4,4'-N-Formyl- and 4,4'-N-Methyl-MDA,
[4]3- and 4-ring isomers,
[5]5-ring and non identifiable products.

Under the same reaction conditions, the modified catalysts revealed a higher content of MMDA compared to the parent sample without treatment. The space-time yield of MMDA is therefore increased.

III.4 Examples 36 to 40 (Comparative, Catalytic Runs with ITQ-2, Amorphous Silica-Alumina and Mesoporous Silica (MCM-41))

For the experiments in examples 35 to 39, aminal "A" was used, the catalyst amount was 0.1 g and the reaction time 4 h resulting in a load of 12.25 $g_{Aminal}/(g_{Catalyst} \cdot h)$.

TABLE 5

Overview of catalytic runs 36 to 40.

| III.4 | Code[1] | ABAs[2] % | MMDA[3] % | PMDA[4] % | Others[5] % | 4,4'-MDA/ 2,4'-MDA |
|---|---|---|---|---|---|---|
| 36 | ASA | 4.7 | 67.2 | 16.9 | 11.2 | 5.4 |
| 37 | ITQ-2 | 11.0 | 60.1 | 6.8 | 22.0 | 3.7 |
| 38 | ITQ-2 | 8.8 | 63.8 | 8.0 | 19.4 | 3.5 |
| 39 | MCM41 | 40.0 | 24.4 | 3.4 | 32.2 | 4.8 |
| 40 | MCM41 | 37.3 | 28.1 | 3.6 | 31.1 | 4.9 |

[1] Code refers to Chapter II, parent zeolite for reference without treatment,
[2] o- and p-ABA,
[3] 4,4'-, 2,4'-, 2,2'-, 4,4'-N-Formyl- and 4,4'-N-Methyl-MDA,
[4] 3- and 4-ring isomers,
[5] 5-ring and non identifiable products The isomer ratio between 4,4'-MDA and 2,4'-MDA is comparably lower than for FAU types. Moreover, the reaction is incomplete.

III.5 Examples 41 to 45 (Comparative, Catalytic Runs with ITQ-2, Amorphous Silica-Alumina and Mesoporous Silica (MCM-41))

For the experiments in examples 41 to 45, aminal "A" was used, the catalyst amount was 1 g and the reaction time 4 h resulting in a load of 1.23 $g_{Aminal}/(g_{Catalyst} \cdot h)$.

TABLE 6

Overview of catalytic runs 41 to 45.

| III.5 | Code[1] | ABAs[2] % | MMDA[3] % | PMDA[4] % | Others[5] % | 4,4'-MDA/ 2,4'-MDA |
|---|---|---|---|---|---|---|
| 41 | ASA | 0.1 | 73.7 | 22.8 | 3.4 | 5.0 |
| 42 | ITQ-2 | 0.1 | 75.2 | 19.1 | 5.7 | 3.6 |
| 43 | ITQ-2 | 1.3 | 78.1 | 16.2 | 4.5 | 3.7 |
| 44 | MCM41 | — | — | — | — | — |
| 45 | MCM41 | — | — | — | — | — |

[1] Code refers to Chapter II, parent zeolite for reference without treatment,
[2] o- and p-ABA,
[3] 4,4'-, 2,4'-, 2,2'-, 4,4'-N-Formyl- and 4,4'-N-Methyl-MDA,
[4] 3- and 4-ring isomers,
[5] 5-ring and non identifiable products.

The isomer ratio between 4,4'-MDA and 2,4'-MDA is comparably lower than for FAU types. Whereas MCM41 revealed poor activity at 0.1 g, it was impossible to filter off the organic phase from the solid catalyst which makes the catalyst impractical for industrial use.

III.6 Examples 46 to 49 (Catalytic Runs with Faujasite-15 and Modifications Thereof)

For the experiments in examples 46 and 47, aminal "A" was used, the catalyst amount was 0.1 g and the reaction time 4 h resulting in a load of 12.25 $g_{Aminal}/(g_{Catalyst} \cdot h)$. For the experiments in examples 48 and 49, aminal "A" was used, the catalyst amount was 1 g and the reaction time 4 h resulting in a load of 1.23 $g_{Aminal}/(g_{Catalyst} \cdot h)$.

TABLE 7

Overview of catalytic runs 46 to 49.

| III.6 | Code[1] | ABAs[2] % | MMDA[3] % | PMDA[4] % | Others[5] % | 4,4'-MDA/ 2,4'-MDA |
|---|---|---|---|---|---|---|
| 46 | FAU15 | 29.2 | 42.0 | 2.3 | 26.4 | 6.5 |
| 47 | II.11 | 3.2 | 69.8 | 17.4 | 9.6 | 5.0 |
| 48 | FAU15 | 0.1 | 83.8 | 14.7 | 1.4 | 7.3 |
| 49 | II.11 | 0.2 | 75.7 | 21.9 | 2.2 | 5.2 |

[1] Code refers to Chapter II, parent zeolite for reference without treatment,
[2] o- and p-ABA,
[3] 4,4'-, 2,4'-, 2,2'-, 4,4'-N-Formyl- and 4,4'-N-Methyl-MDA,
[4] 3- and 4-ring isomers,
[5] 5-ring and non identifiable products.

A higher space-time yield on higher homologues of modified Faujasite-15 compared to the parent one was obtained.

III.7 Examples 50 to 55 (Catalytic Runs with Faujasite-6 and Modifications Thereof)

For the experiments in examples 50 and 55, aminal "A" was used, the catalyst amount was 0.1 g and the reaction time 1 h resulting in a load of 49.00 $g_{Aminal}/(g_{Catalyst} \cdot h)$.

TABLE 8

Overview of catalytic runs 50 to 55.

| III.7 | Code[1] | ABAs[2] % | MMDA[3] % | PMDA[4] % | Others[5] % | 4,4'-MDA/ 2,4'-MDA |
|---|---|---|---|---|---|---|
| 50 | FAU6 | 55.3 | 10.1 | 0.2 | 34.4 | 6.3 |
| 51 | FAU6 | 55.6 | 9.7 | 0.2 | 34.5 | 6.3 |
| 52 | II.1 | 41.4 | 26.2 | 0.9 | 31.4 | 6.0 |
| 53 | II.1 | 39.8 | 28.6 | 1.1 | 30.5 | 6.0 |
| 54 | II.2 | 13.3 | 63.1 | 5.8 | 17.7 | 6.2 |
| 55 | II.2 | 15.6 | 59.8 | 5.4 | 19.2 | 6.2 |

[1] Code refers to Chapter II, parent zeolite for reference without treatment,
[2] o- and p-ABA,
[3] 4,4'-, 2,4'-, 2,2'-, 4,4'-N-Formyl- and 4,4'-N-Methyl-MDA,
[4] 3- and 4-ring isomers,
[5] 5-ring and non identifiable products A higher space-time yield on MMDA and higher homologues of modified FAU-6 compared to the parent one was obtained.

III.8 Examples 56 to 72 (Catalytic Runs Varying A/F Ratio)

For the experiments in examples 56 to 60, aminal "C" was used, the catalyst amount was 1 g and the reaction time 4 h resulting in a load of 1.23 $g_{Aminal}/(g_{Catalyst} \cdot h)$. For the experiments in examples 61 to 66, aminal "B" was used, the catalyst amount was 1 g and the reaction time 4 h resulting in a load of 1.23 $g_{Aminal}/(g_{Catalyst} \cdot h)$. For the experiments in examples 67 to 72, aminal "A" was used, the catalyst amount was 1 g and the reaction time 4 h resulting in a load of 1.23 $g_{Aminal}/(g_{Catalyst} \cdot h)$.

TABLE 9

Overview of catalytic runs 56 to 72.

| III.8 | Code[1] | ABAs[2] % | MMDA[3] % | PMDA[4] % | Others[5] % | 4,4'-MDA/ 2,4'-MDA |
|---|---|---|---|---|---|---|
| 56 | FAU6 | 0.6 | 71.5 | 16.6 | 11.3 | 5.6 |
| 57 | II.1 | 0.1 | 69.5 | 25.1 | 5.3 | 4.7 |
| 58 | II.1 | 0.2 | 69.6 | 25.0 | 5.2 | 4.7 |
| 59 | II.2 | 0.1 | 64.4 | 30.7 | 4.9 | 5.2 |
| 60 | II.2 | 0.1 | 64.8 | 30.6 | 4.6 | 5.3 |
| 61 | FAU6 | 0.0 | 77.1 | 18.6 | 4.3 | 6.7 |
| 62 | FAU6 | 0.0 | 79.1 | 17.1 | 3.8 | 6.7 |
| 63 | II.1 | 0.1 | 75.2 | 22.2 | 2.6 | 5.1 |
| 64 | II.1 | 0.5 | 74.9 | 21.5 | 3.1 | 5.2 |
| 65 | II.2 | 0.2 | 72.7 | 24.4 | 2.7 | 5.4 |

TABLE 9-continued

Overview of catalytic runs 56 to 72.

| III.8 | Code[1] | ABAs[2] % | MMDA[3] % | PMDA[4] % | Others[5] % | 4,4'-MDA/ 2,4'-MDA |
|---|---|---|---|---|---|---|
| 66 | II.2 | 0.1 | 73.2 | 24.1 | 2.7 | 5.3 |
| 67 | FAU6 | 0.0 | 82.7 | 15.7 | 1.6 | 6.4 |
| 68 | FAU6 | 0.0 | 83.6 | 14.8 | 1.7 | 6.5 |
| 69 | II.1 | 0.0 | 81.7 | 16.9 | 1.4 | 5.9 |
| 70 | II.1 | 0.0 | 81.8 | 16.8 | 1.4 | 5.9 |
| 71 | II.2 | 0.4 | 73.8 | 23.1 | 2.7 | 5.1 |
| 72 | II.2 | 0.0 | 76.0 | 21.6 | 2.4 | 5.3 |

[1] Code refers to Chapter II, parent zeolite for reference without treatment,
[2] o- and p-ABA,
[3] 4,4'-, 2,4'-, 2,2'-, 4,4'-N-Formyl- and 4,4'-N-Methyl-MDA,
[4] 3- and 4-ring isomers,
[5] 5-ring and non identifiable products At varying A/F ratio, a higher space-time yield on MMDA and higher homologues of modified FAU-6 compared to the parent one was obtained.

The invention claimed is:

1. A process for the preparation of di- and polyamines of the diphenylmethane series comprising rearranging a condensation product, wherein said condensation product is formed by reacting aniline and a methylene group-supplying agent, and wherein said condensation product is reacted in the presence of at least one solid zeolite catalyst which is partially or fully ion-exchanged to the protonic form and comprises
   A) at least one alkaline-treated zeolite catalyst, wherein the alkaline treatment of BEA zeolites is carried out in the presence of a pore-directing agent and the alkaline treatment of zeolites other than BEA zeolites is carried out in the presence or absence of a pore-directing agent.

2. The process according to claim 1, wherein said alkaline-treated zeolite catalyst A) is selected from the group consisting of:
   (i) zeolites other than BEA zeolites which have been alkaline-treated in the presence or absence of a pore-directing agent;
   (ii) BEA zeolites which have been alkaline-treated in the presence of a pore-directing agent;
   (iii) zeolites which have been acid-treated in a first step and alkaline-treated in a second step;
   (iv) zeolites which have been alkaline-treated in a first step and acid-treated in a second step;
   (v) zeolites which have been acid-treated in a first step, alkaline treated in a second step and acid-treated in a third step;
   and
   (vi) mixtures thereof.

3. The process according to claim 1, wherein said pore-directing agent comprises an alkylammonium cation having the general molecular formula $^+NR^i_4$, wherein the four $R^i$ substituents can be the same or different and can be selected from the group consisting of organic substituents and hydrogen.

4. The process according to claim 1, wherein said at least one-solid zeolite catalyst comprises a FAU type zeolite.

5. The process according to claim 2, wherein said alkaline-treated zeolite catalyst A) comprises (i) a zeolite other than a BEA zeolite in which the alkaline treatment is carried out in a pH range of 10 to 15 using an alkali metal hydroxide solution at a temperature of from 10° C. to 100° C. for a period of from 0.1 minutes to 180 minutes with a zeolite loading of 5 g L$^{-1}$ to 400 g L$^{-1}$, in which "L" refers to the volume of the total reaction mixture.

6. The process according to 2, wherein said alkaline-treated zeolite catalyst A) comprises (ii) a BEA zeolite in which the alkaline treatment is carried out in a pH range of 10 to 15 using an alkali metal hydroxide solution at a temperature of from 10° C. to 100° C. for a period of from 0.1 minutes to 180 minutes with a zeolite loading of 5 g L$^{-1}$ to 400 g L$^{-1}$, in which "L" refers to the volume of the total reaction mixture.

7. The process according to claim 2, wherein said alkaline-treated zeolite catalyst A) comprises (iii) a zeolite in which the acid treatment is carried out using an aqueous solution of an organic acid with chelating function or an aqueous solution of a mineral acid having a concentration of 0.01 mol L$^{-1}$ to 1 mol L$^{-1}$ at a temperature of from 10° C. to 100° C for a period of from 0.25 hours to 100 hours.

8. The process according to claim 7, wherein said alkaline-treated zeolite catalyst A) comprises (iii) a zeolite in which the alkaline treatment following the acid treatment is carried out in a pH range of 10 to 15 using an alkali metal hydroxide solution at a temperature of from 10° C. to 100° C. for a period of from 0.1 minutes to 180 minutes with a zeolite loading of 5 g L$^{-1}$ to 400 g L$^{-1}$, in which "L" refers to the volume of the total reaction mixture.

9. The process according to claim 2, wherein said alkaline-treated zeolite catalyst A) comprises (iv) a zeolite in which the alkaline treatment is carried out in a pH range of 10 to 15 using an alkali metal hydroxide solution at a temperature of from 10° C. to 100° C. for a period of from 0.1 minutes to 180 minutes with a zeolite loading of 5 g L$^{-1}$ to 400 g L$^{-1}$, in which "L" refers to the volume of the total reaction mixture.

10. The process according to claim 9, wherein said alkaline-treated zeolite catalyst A) comprises (iv) a zeolite in which the acid treatment following the alkaline treatment is carried out using an aqueous solution of an organic acid with chelating function or an aqueous solution of a mineral acid having a concentration of 0.01 mol L$^{-1}$ to 1 mol L$^{-1}$ at a temperature of from 10° C. to 100° C. for a period of from 0.25 hours to 100 hours.

11. The process according to claim 2, wherein said alkaline-treated zeolite catalyst A) comprises (v) a zeolite in which both acid treatments are carried out using an aqueous solution of an organic acid with chelating function or an aqueous solution of a mineral acid having a concentration of 0.01 mol L$^{-1}$ to 1 mol L$^{-1}$ at a temperature of from 10° C. to 100° C. for a period of from 0.25 hours to 100 hours.

12. The process according to claim 11, wherein said alkaline-treated zeolite catalyst A) comprises (v) a zeolite in which the alkaline treatment between the acid treatments is carried out in a pH range of 10 to 15 using an alkali metal hydroxide solution at a temperature of from 10° C. to 100° C. for a period of from 0.1 minutes to 180 minutes with a zeolite loading of 5 g L$^{-1}$ to 400 g L$^{-1}$, in which "L" refers to the volume of the total reaction mixture.

13. The process according to claim 1, wherein the treatment of alkaline-treated zeolite catalysts A) is performed such that the zeolite catalyst obtained after completion of the treatment has a crystallinity as determined by X-ray diffraction analysis of at least 50% when compared to the parent zeolite catalyst before the respective treatment.

14. The process of claim 1, wherein said methylene group supplying agent is selected from the group consisting of aqueous formaldehyde solution, gaseous formaldehyde, para-formaldehyde, trioxane and mixtures thereof.

* * * * *